(12) United States Patent
Gerondale et al.

(10) Patent No.: US 7,641,637 B2
(45) Date of Patent: *Jan. 5, 2010

(54) CONTROLLED VOLUME INJECTION/ASPIRATION DEVICE

(75) Inventors: Scott J. Gerondale, Mission Viejo, CA (US); Steven D. Kimmell, Granada Hills, CA (US); Jeffrey Field, Camarillo, CA (US)

(73) Assignee: Allergan, Inc, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/108,409

(22) Filed: Apr. 23, 2008

(65) Prior Publication Data

US 2008/0200882 A1 Aug. 21, 2008

Related U.S. Application Data

(63) Continuation of application No. 10/824,970, filed on Apr. 15, 2004, now Pat. No. 7,364,570.

(60) Provisional application No. 60/463,638, filed on Apr. 16, 2003.

(51) Int. Cl.
*A61M 5/00* (2006.01)
*A61M 5/315* (2006.01)

(52) U.S. Cl. ....................... 604/209; 604/224

(58) Field of Classification Search ........... 604/224, 604/232, 218, 208–209, 211; 600/578
See application file for complete search history.

(56) References Cited

U.S. PATENT DOCUMENTS

| | | | |
|---|---|---|---|
| 780,147 A | 1/1905 | Wilcox |
| 854,399 A | 5/1907 | Bridge |
| 1,718,596 A | 6/1929 | Smith |
| 2,718,299 A | 9/1955 | Atwater |
| 2,892,457 A | 6/1959 | Sturtz |
| 3,102,539 A | 9/1963 | Goldberg |
| 3,517,668 A | 6/1970 | Brickson |
| 3,977,574 A | 8/1976 | Thomas |
| 4,022,207 A | 5/1977 | Citrin |
| 4,099,548 A | 7/1978 | Sturm |
| 4,364,388 A | 12/1982 | Cech |
| 4,395,921 A | 8/1983 | Oppenlander |
| 4,424,055 A | 1/1984 | Herman |
| 4,457,712 A | 7/1984 | Dragan |
| 4,465,478 A | 8/1984 | Sabelman |

(Continued)

FOREIGN PATENT DOCUMENTS

DE 3408618 A1 9/1985

*Primary Examiner*—Kevin Sirmons
*Assistant Examiner*—Andrew M Gilbert
(74) *Attorney, Agent, or Firm*—Allergan, Inc.; Dean G. Stathakis

(57) ABSTRACT

A controlled volume injection/aspiration device includes a syringe having a body for containing a medicament, a needle and a piston slidably disposed within the body. A shell is provided for receiving the syringe body and a plunger rack is disposed within the shell. A manually operated control is disposed in an operative relationship with the plunger rack for moving the plunger rack in a stepwise forward direction causing the piston to eject discrete doses of medication from the syringe body through the needle. The manual operated control is also operative for moving the piston in a stepwise reverse direction causing the piston to aspirate fluid into the syringe body through the needle.

6 Claims, 2 Drawing Sheets

U.S. PATENT DOCUMENTS

| | | |
|---|---|---|
| 4,592,745 A | 6/1986 | Rex |
| 4,710,178 A | 12/1987 | Henri et al. |
| 4,865,591 A | 9/1989 | Sams |
| 4,883,472 A | 11/1989 | Michel |
| 4,936,833 A | 6/1990 | Sams |
| 4,950,246 A | 8/1990 | Muller |
| 4,973,318 A | 11/1990 | Holm |
| 5,017,190 A | 5/1991 | Simon |
| 5,112,317 A | 5/1992 | Michel |
| 5,279,586 A | 1/1994 | Balkwill |
| 5,378,233 A | 1/1995 | Haber |
| 5,507,727 A | 4/1996 | Crainich |
| 5,674,205 A | 10/1997 | Pasricha |
| 5,714,468 A | 2/1998 | Binder |
| 5,782,633 A | 7/1998 | Muhlbauer |
| 5,807,340 A | 9/1998 | Pokras |
| 5,891,106 A | 4/1999 | Butuzov |
| 6,007,515 A | 12/1999 | Epstein |
| 6,102,895 A | 8/2000 | Cortella |
| 6,159,161 A | 12/2000 | Hodosh |
| 7,364,570 B2 * | 4/2008 | Gerondale et al. .......... 604/209 |
| 2006/0217670 A1 | 9/2006 | Cecchi |

* cited by examiner

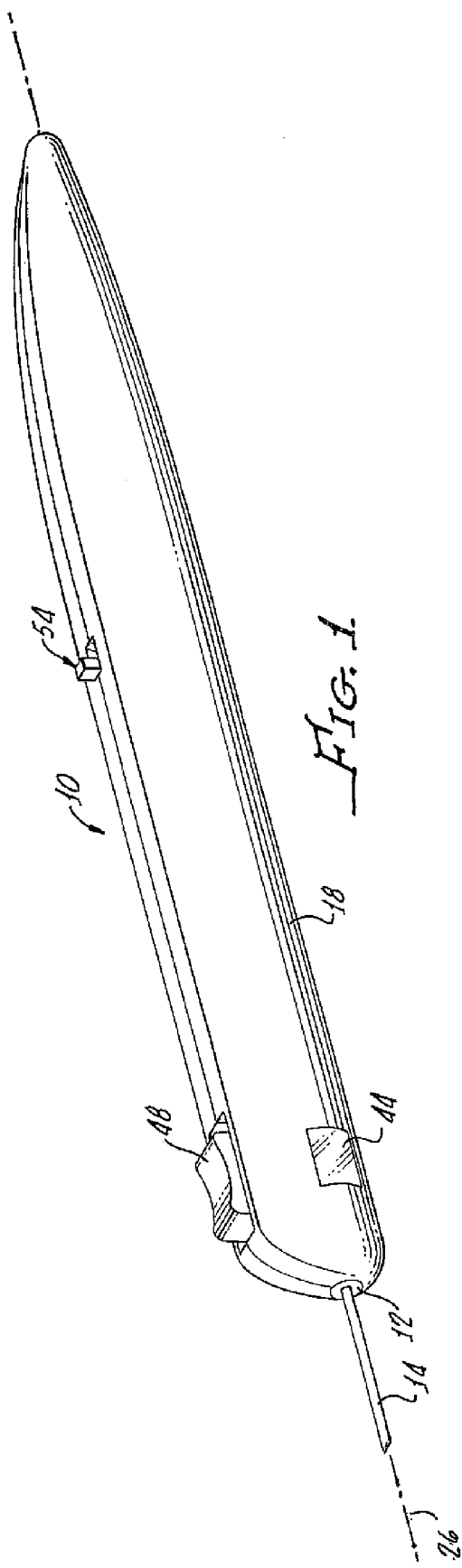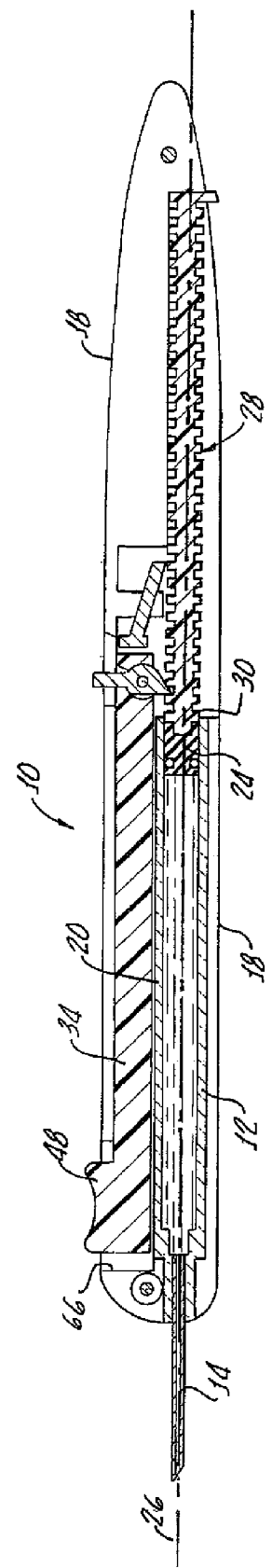

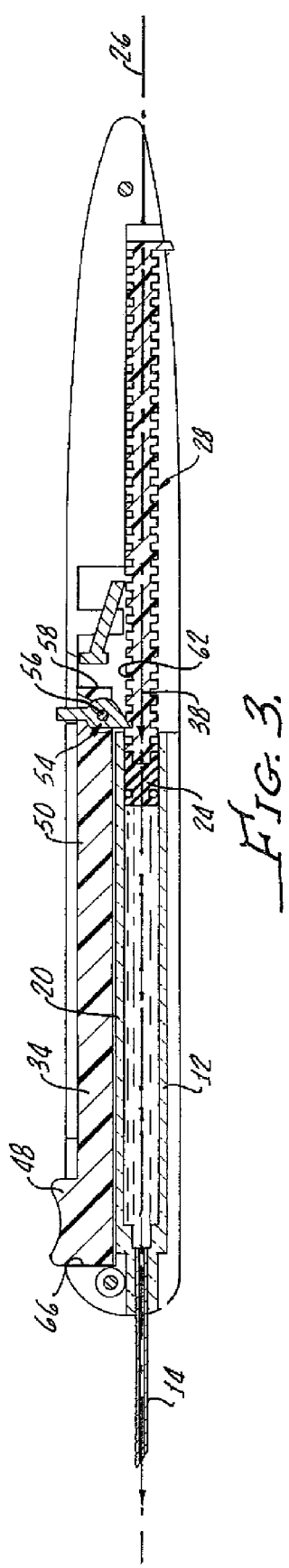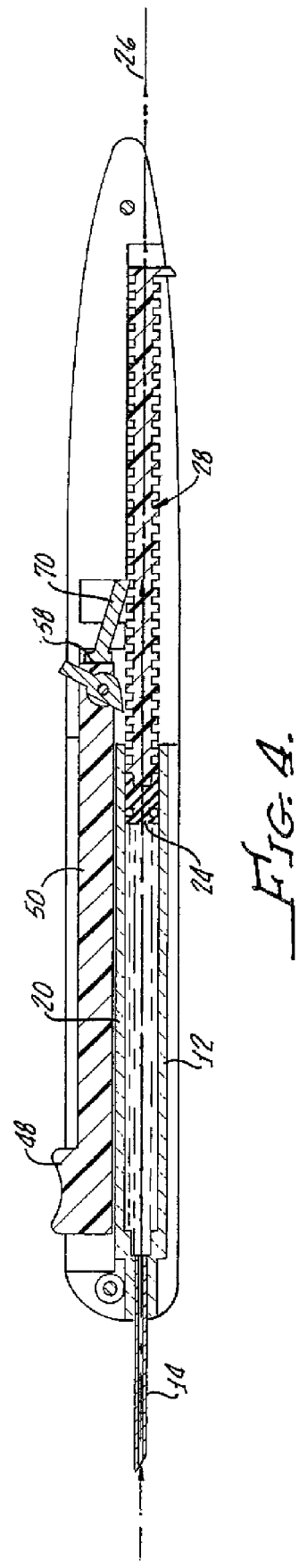

CONTROLLED VOLUME INJECTION/ASPIRATION DEVICE

The present application is a continuation of U.S. Ser. No. 10/824,970 filed Apr. 15, 2004 now U.S. patent Ser. No. 7,364,570 which claims priority from U.S. Provisional Patent Application Ser. No. 60/463,638 filed Apr. 16, 2003 both these references are to be incorporated herewith in their entirety by this specific reference thereto.

The present invention is generally directed to a multiple dosage injection device and more particularly to a multiple dosage injection dispensing pen which is suitable for precise placement of desired amounts of BOTOX® to specific muscle tissue.

Current procedures for injection of BOTOX® utilize a syringe and the injection volume is controlled by a users, ability to stop on graduations indicated on a side of the syringe.

Local administration of a chemodenervating agent, such as botulinum toxin, often is performed through subcutaneous, intramuscular, paramuscular injection, or percutaneous installation. When the chemodenervating agent is injected by subcutaneous injection the agent reaches the muscle by perfusion.

Typically, a multiple number of small injections is utilized to treat a specific area with each injection being in the range of between about 5 microliters and about 1 ml.

As hereinabove noted, heretofore procedures utilizing conventional syringes have difficulty in controlling small injectionable amounts with the consistency.

The present invention provides for a controlled volume injection/aspiration device for the effective administration of a chemodenervating agent, such as botulinum toxin, to a selected area.

SUMMARY OF THE INVENTION

A controlled volume injector/withdrawal device in accordance with the present invention generally includes a syringe having a body for containing a medicament, a needle and a piston slidably disposed in the body.

A shell is provided for receiving syringe body with a needle projecting from the shell. A plunger rack disposed within the shell is slidable for moving of the piston and a manually operated control is disposed in an operative relationship with the plunger rack for moving the plunger rack in a stepwise forward direction causing the piston to eject medication from the syringe body through the needle and a stepwise reverse direction causing the piston to aspirate fluid into the syringe body through the needle.

More particularly, the device may include a window disposed in the shell for enabling observation of fluid aspirated into the syringe body. This feature enables the user to determine needle placement by such aspiration. For example, if, upon aspiration, blood appears visible through the window the user physician would change placement of the needle tip in order to avoid injecting BOTOX® directly into a blood vessel.

More particularly, the control comprises an injecting pawl for engaging the plunger rack for moving the plunger rack in the stepwise forward direction and disengaging the plunger rack upon movement in the stepwise reverse direction.

In addition, a withdrawing pawl is provided for engaging the plunger rack for moving the plunger rack in the stepwise reverse direction and disengaging the plunger rack upon movement in the stepwise forward direction.

The control is configured, through rack and pawl sizing, for injecting medication in the range between about 5 μl and about 1 ml.

Preferably, the control is configured for finger operation so that that entire injection and aspiration process can be carried out through a one handed operation. In addition, the syringe may be of conventional design or specific BOTOX® design and is removable from the shell. In that regard, the invention further includes separately the shell, plunger rack and manually operated control.

BRIEF DESCRIPTION OF THE DRAWINGS

The present invention may be more clearly understood with reference to the following detailed description in conjunction with the appended drawings of which:

FIG. 1 is a perspective view of the controlled volume injection/withdrawal device in accordance with the present invention generally showing a needle projecting from a shell and a manually engagable trigger;

FIG. 2 is a cross sectional view of the device shown in FIG. 1 illustrating a syringe body disposed within the device shell with the needle projecting therefrom along with an operating control shown in a neutral position with injecting and withdrawing pawls for selectively engaging a plunger rack which operates a piston for both ejecting medicine from the syringe body and aspirating fluid into the syringe body;

FIG. 3 is a view of the device shown in FIGS. 1 and 2 during an injecting procedure in which the trigger is moved in a forward direction and the injecting pawl engages the plunger rack for movement of the piston in a forward direction; and FIG. 4 is a view of the device similar to FIGS. 1-3 illustrating withdrawal or aspiration of fluid from a body (not shown) when the trigger is moved in a reverse direction and the withdrawing pawl engages the plunger rack.

DETAILED DESCRIPTION

With reference to FIG. 1, there is shown a control volume injection/aspiration device 10 in accordance with the present invention generally showing a syringe 12 and needle 14 along with a shell 18 for receiving a syringe body 20, see FIGS. 2-4.

As shown in FIGS. 2-4, the syringe 12 includes a piston 24 slidably disposed in the syringe body 24 for forcing medicament through the needle 14. A plunger rack 28 is slidably disposed within the shell 18 and coupled to the piston 24 at a front end 30 thereof.

A manually operated control 34 is disposed in an operative relationship with the plunger rack 28, as hereinafter described in greater detail, for moving the plunger rack 28 in a forward direction, indicated by arrow 38 in FIG. 3, causing the piston 24 to eject discrete doses of medication from the syringe body 20 through the needle 14, and move the piston 24 in a reverse direction, indicated by the arrow 40, in FIG. 4 to aspirate discrete quantities of fluid into the syringe body 20 through the needle 14.

A window 44 is provided in the shell 18 in order to observe withdrawn, or aspirated fluid from a body, not shown. As hereinabove noted, this reverse motion of the piston for aspirating fluids from a body prior to injection will give an indication of proper placement of the needle for injection of the medicament, preferably botulinum toxin.

The operating control 34 includes a button 48 manually accessible from outside of the shell 18 and a control rod 50 an injecting pawl 54 is pivot 56 mounted to an end 58 of the rod and is limited in rotation so that forward motion of the button 48 from a neutral position, as shown in FIG. 2, causes the injecting pawl 54 to engage plunger rack teeth 62.

Forward movement of the plunger rack 28 and piston 24 is limited to a discrete amount defined by the spacing between the button 48 and a front face 66 of the shell 18. Thus, movement of the button forward in a direction of the arrow 38 causes a limited or discrete movement of the plunger rack and piston thereby causing a discrete measured dose of medicament to be ejected through the needle 14.

Reverse movement of the button 48 and rod from the position shown in FIG. 3 to a neutral position, shown in FIG. 2, causes the injecting pawl to ride over the teeth 62. The injecting pawl 54 again engages the teeth 62 as the button 48 is moved forward again in the direction of arrow 38.

Thus, repeated discrete amounts of medicament can be injected into a selected area (not shown) of a patient (not shown). Such discrete doses are preferably within the range of about 5 microliters and about 1 ml with such doses being defined by the movement available by the button 48.

With reference to FIG. 4, when the button 48 is moved in the direction of the arrow 40 past the neutral position, shown in FIG. 2, the rod end engages a withdrawing pawl and engages the pawl 70 with the rack teeth 62 by rotation about a pivot 72. In this movement, the injecting pawl 54 is disengaged from the rack teeth 62. This movement causes withdrawal of the piston from the body 20 and aspiration of fluid through the needle 14 and into the syringe body 20 which may be observed through the window 44.

The injection/aspiration device 10 may be precharged with botulinum toxin and disposable or alternatively the syringe 12 may be removable from the shell 19. In this embodiment recharged syringes 12, along with needles, may be provided with the shell 18 and the operating control 34 utilized for subsequent multiple injections of botulinum toxin.

It should also be appreciated that the elements of the present invention may be formed from any suitable materials for use in medical applications.

Although there has been hereinabove described a specific controlled volume injection/aspiration device in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A controlled volume injection/aspiration device comprising:
    a syringe having a body for containing a medicament, a needle and a piston slidably disposed in said body along a body centerline;
    a plunger rack slidably disposed along the body centerline for moving said piston along the body centerline;
    a manually operated control rod disposed in an operative parallel relationship with said centerline, and slidable therealong, for providing stepwise movement of said plunger rack in a forward direction causing said piston to eject discrete doses of medication from said syringe body through said needle and stepwise movement of said plunger rack in a reverse direction causing said piston to aspirate discrete quantities of fluid into said syringe body through said needle;
    an injecting pawl, connected to said control rod, for engaging said plunger rack and moving said plunger rack in said stepwise forward direction and disengaging said plunger rack upon movement in said stepwise reverse direction; and
    a button for sliding the control rod parallel to the body centerline, movement in one direction causing ejection of medicament and movement in an opposite direction causing aspiration of fluid.

2. The device according to claim 1 further comprising a window disposed in said shell for enabling observation of fluid aspirated into the syringe body.

3. The device according to claim 1 further comprising a withdrawing pawl, connected to said control rod, for engaging said plunger rack and moving said plunger rack in said stepwise reverse direction and disengaging said plunger each upon movement in said stepwise forward direction.

4. The device according to claim 1 wherein the medicament comprises botulinum toxin.

5. The device according to claim 1 wherein said syringe is removable from the said shell.

6. A controlled volume injection/aspiration device comprising:
    a syringe having a body for containing a medicament, a needle and a piston slidably disposed in said body along a body centerline;
    a plunger rack slidably disposed along the body centerline for moving said piston along the body centerline;
    a control rod disposed in a parallel relationship with the body centerline, and slidable therealong;
    an injecting pawl, pivotal mounted to an end of said control rod, for engaging said plunger rack for moving said plunger rack in a forward direction upon forward movement of said control rod and disengaging said plunger rack upon movement of said control rod in a reverse direction;
    a withdrawing pawl for engaging the control rod end and further engaging said plunger rack for moving said plunger rack each in a reverse direction and disengaging said plunger each upon movement in said forward direction; and
    a button for sliding the control rod parallel to the body centerline.

* * * * *